United States Patent
Van Dyke

(10) Patent No.: US 6,914,126 B2
(45) Date of Patent: Jul. 5, 2005

(54) METHODS FOR PRODUCING, FILMS COMPRISING, AND METHODS FOR USING HETEROGENOUS CROSSLINKED PROTEIN NETWORKS

(75) Inventor: Mark E. Van Dyke, Fair Oaks Ranch, TX (US)

(73) Assignee: Keraplast Technologies, Ltd., San Antonio, TX (US)

(*) Notice: Subject to any disclaimer, the term of this patent is extended or adjusted under 35 U.S.C. 154(b) by 229 days.

(21) Appl. No.: 10/119,477

(22) Filed: Apr. 10, 2002

(65) Prior Publication Data

US 2003/0219486 A1 Nov. 27, 2003

(51) Int. Cl.$^7$ ................................................ C08H 1/06
(52) U.S. Cl. ........................ 530/357; 514/12; 530/350; 530/356; 530/409; 530/410; 530/842
(58) Field of Search ........................... 514/12; 530/350, 530/356, 357, 409, 410, 842

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 2,434,688 A | 1/1948 | Evans | |
| 3,250,682 A | 5/1966 | Wilmsmann et al. | |
| 3,642,498 A | 2/1972 | Anker | |
| 3,677,693 A | 7/1972 | Fillingham | |
| 3,842,848 A | 10/1974 | Karjala | 424/71 |
| 4,041,150 A | 8/1977 | Karjala | 424/71 |
| 4,279,996 A | 7/1981 | Yoshioka et al. | 435/69 |
| 4,423,032 A | 12/1983 | Abe et al. | |
| 4,474,694 A | 10/1984 | Coco et al. | |
| 4,495,173 A | 1/1985 | Matsunaga et al. | |
| 4,504,644 A | 3/1985 | Lang et al. | |
| 4,570,629 A | 2/1986 | Widra | |
| 4,659,566 A | 4/1987 | Petrow | 424/71 |
| 4,751,074 A | 6/1988 | Matsunaga et al. | |
| 4,895,722 A | 1/1990 | Abe et al. | |
| 4,906,460 A | 3/1990 | Kim et al. | 424/70 |
| 4,959,213 A | 9/1990 | Brod et al. | 514/21 |
| 5,047,249 A | 9/1991 | Rothman et al. | |
| 5,073,294 A | 12/1991 | Shannon et al. | |
| 5,202,053 A | 4/1993 | Shannon | |
| 5,219,562 A | 6/1993 | Fujiu et al. | 424/71 |
| 5,258,501 A | 11/1993 | Barbaric et al. | |
| 5,276,138 A | 1/1994 | Yamada et al. | |
| 5,288,489 A * | 2/1994 | Reich et al. | 424/94.64 |
| 5,300,285 A | 4/1994 | Halloran et al. | |
| 5,356,433 A | 10/1994 | Rowland et al. | |
| 5,358,935 A | 10/1994 | Smith et al. | 514/21 |
| 5,412,076 A | 5/1995 | Gagnieu | |
| 5,424,062 A | 6/1995 | Schwan et al. | 424/70.5 |
| 5,425,937 A | 6/1995 | Uchiwa et al. | 424/70.14 |
| 5,444,154 A * | 8/1995 | O'Lenick, Jr. | 530/356 |
| 5,505,952 A | 4/1996 | Jiang et al. | |
| 5,520,925 A | 5/1996 | Maser | |
| 5,563,230 A | 10/1996 | Hsu et al. | |
| 5,654,471 A | 8/1997 | Zahn et al. | |
| 5,679,819 A | 10/1997 | Jones et al. | |
| 5,712,252 A | 1/1998 | Smith | |
| 5,833,880 A | 11/1998 | Siemensmeyer | |
| 5,932,552 A | 8/1999 | Blanchard et al. | |
| 5,942,009 A | 8/1999 | Burns | 8/432 |
| 5,948,432 A | 9/1999 | Timmons et al. | 424/443 |
| 5,955,549 A | 9/1999 | Chang et al. | |
| 5,989,461 A | 11/1999 | Coates et al. | |
| 6,087,462 A | 7/2000 | Bowers et al. | |
| 6,090,308 A | 7/2000 | Coates et al. | |
| 6,110,487 A | 8/2000 | Timmons et al. | 424/443 |
| 6,124,265 A | 9/2000 | Timmons et al. | 424/443 |
| 6,140,475 A * | 10/2000 | Margolin et al. | 530/402 |
| 6,159,495 A | 12/2000 | Timmons et al. | 424/443 |
| 6,159,496 A | 12/2000 | Blanchard | |
| 6,165,496 A | 12/2000 | Timmons et al. | 424/443 |
| 6,211,296 B1 | 4/2001 | Frate et al. | |
| 6,270,791 B1 | 8/2001 | Van Dyke et al. | 424/443 |
| 6,270,793 B1 | 8/2001 | Van Dyke et al. | 424/443 |
| 6,274,155 B1 | 8/2001 | Van Dyke et al. | 424/402 |
| 6,274,163 B1 | 8/2001 | Blanchard et al. | 424/443 |
| 6,280,474 B1 * | 8/2001 | Cassidy et al. | 623/16.11 |
| 6,303,150 B1 * | 10/2001 | Perrier et al. | 424/491 |
| 6,316,598 B1 | 11/2001 | Van Dyke et al. | |
| 6,352,699 B1 | 3/2002 | Mondet et al. | |
| 6,361,767 B1 | 3/2002 | Malle et al. | |
| 6,371,984 B1 | 4/2002 | Van Dyke et al. | |
| 6,379,690 B2 | 4/2002 | Blanchard et al. | |
| 6,399,051 B2 | 6/2002 | Dannecker et al. | |
| 6,432,435 B1 | 8/2002 | Timmons et al. | |
| 6,435,193 B1 | 8/2002 | Cannell et al. | |
| 6,461,628 B1 | 10/2002 | Blanchard et al. | |
| 6,565,842 B1 * | 5/2003 | Desai et al. | 424/85.1 |

FOREIGN PATENT DOCUMENTS

| | | |
|---|---|---|
| EP | 0097907 | 1/1984 |
| EP | 0 298 684 A3 | 1/1989 |
| EP | 0454 600 A1 | 10/1991 |
| EP | 0 468 797 A2 | 1/1992 |
| EP | 0540357 | 5/1993 |
| JP | 4-189833 | 7/1992 |
| JP | 2002-113815 | 4/2002 |
| WO | WO 93/10827 | 6/1993 |
| WO | WO 93/22397 | 11/1993 |
| WO | WO 98/ 08550 | 3/1998 |
| WO | WO 9931167 | 6/1999 |
| WO | WO 03008006 | 1/2003 |

OTHER PUBLICATIONS

Nagase Chemtex product information on Denacols, 2001.*
Feughelman et al., "Structural features of keratin suggested by its mechanical properties," Biochim. Biophys. Acta (1959), 32, 596–7 (Chem. Abstracts 53: 15156b–c).*
S. F. Sadova and A. A. Konkin. Grafting of vinyl monomers onto wool keratin in an oxidation–reduction system. Zh Vses Khim O–va 1967; 12(5):596–7.

(Continued)

*Primary Examiner*—Robert A. Wax
(74) *Attorney, Agent, or Firm*—Vinson & Elkins L.L.P.

(57) ABSTRACT

Methods for producing biocompatible heterogeneous proteinaceous networks crosslinked with a heterogeneous crosslinking agent, and the novel crosslinked networks.

12 Claims, No Drawings

OTHER PUBLICATIONS

Iwata, et al.; Coating Film For Living Tissues; Nov. 2, 1985; total of 9 pages; Japanese Patent Application Kokai Publication No. Sho 60–220068.

Yoshioka et al; Modified Animal Hair or Wool Powder, Jul. 11, 1989; total of 13 pages; Japanese Unexamined Patent Application Publication H01–174528.

Miyamoto et al; Process for Producing Modified Keratin Protein; Feb. 6, 1982; total of 4 pages; Japanese Patent Application Kokai Publication No. Sho 57–23631.

Yamauchi et al; Keratin Microcapsule, Production of Keratin Microcapsules, and Cosmetics Containing Keratin Microcapsules; Dec. 22, 1998; total of 5 pages; Japanese Patent Application Kokai Publication No. H10–337466.

J.M. Gillespie, et al., "Amino Acid composition of a Sulphur–Rich Protein from Wool," Biochim. Biophy. Acta, (1960) pp. 538–539; vol. 39.

Keith H. Gough, et al., "Amino Acid Sequences of alpha–Helical Segments from S–Carboxymethylkerateine–A: Complete Sequence of a Type–I Segment," Biochem. J. (1978), pp. 373–385; vol. 173.

Thomas C. Elleman, et al., "Amino Acid Sequences of alpha–Helical Segments from S–Carboxymethylkerateine–A:. Statistical Analysis," Biochem. J. (1978), pp. 387–391, vol. 173.

David McC. Hogg, et al., "Amino Acid Sequences of alpha–Helical Segments from S–Carboxymethlkerateine–A:. Tryptic and Chymotryptic Peptides from a Type–II Segment," Biochem. J. (1978), pp. 353–363; vol. 173.

W. Gordon Crewther, et al., "Amino Acid Sequences of alpha–Helical Segments from S–Carboxymethylkerateine–A: Complete Sequence of a Type–II Segment," Biochem. J. (1978), pp. 365–371; vol. 173.

C. Earland, et al., "Studies on the Structure of Keratin: II. The Amino Acid Context of Fractions Isolated from Oxidized Wool," Biochemica et Biophysica Acta (1956), pp. 405–411, vol. 22.

J.M. Gillespie, et al., "Preparation of an Electrophoretically Homogeneous Keratin Derivative from Wool," Short Communications, Preliminary Notes, (1953), pp. 481–482, vol. 12.

Maurice J. Frenkel, et al., "The Isolation and Properties of a Tyrosine–Rich Protein from Wool: Component 0.62," Eur. J. Biochem, (1973) pp. 112–119, vol. 34.

R.J. Blagrove, et al., "The Electrophoresis of the High–Tyrosine Proteins of Keratins on Cellulose Acetate Strips," Comp. Biochem. Physiol., (1975) pp. 571–572, vol. 50B.

Robert C. Marshall, et al., "Successful Isoelectric Focusing of Wool Low–Sulphur Proteins," Journal of Chromatography, (1979) pp. 351–356, vol. 172.

Robert C. Marshall, "Characterization of the Proteins of Human Hair and Nail by Electrophoresis," The Journal of Investigation Dermatology, (1983) pp. 519–524, vol. 80.

W. G. Crewther, et al. "Helix–Rich Fraction from the Low–Sulphur Proteins of Wool," Nature, (Jul. 17, 1965) p. 295, No. 4994.

H. Lindley, et al., "Occurrence of the Cys–Cys Sequence in Keratins," J. Mol. Biol., (1967) pp. 63–67, vol. 30.

Robert C. Marshall, "Genetic Variation in the Proteins of Human Nail," The Journal of Investigative Dermatology, (1980) pp. 264–269, vol. 75.

M. E. Campbell, et al., "Compositional Studies of High–and Low–Crimp Wools," Aust. J. Biol. Sci., (1972) pp. 977–987, vol. 25.

P.J Reis, et al. "A Relationship between Sulphur Content of Wool and Wool Production by Merino Sheep," Aust. J. Biol. Sci., (1967) pp. 153–163, vol. 20.

Robert C. Marshall, et al., "The Keratin Proteins of Wool, Horn and Hoof from Sheep," Aust. J. Biol. Sci, (1977) pp. 389–400, vol. 30.

J.M. Gillespie. "Reaction of Sodium Borohydride with Wool," Nature, (Jan. 31, 1959) pp. 322–323, vol. 183.

David R. Goddard, et al., "A Study on Keratin," J. Bio. Chem., (1934) pp. 605–614, vol. 106.

L.M. Dowling, et al., "Isolation of Components from the Low–Sulphur Proteins of Wool by Fractional Preciptation Preparative Biochemistry," (1974) pp. 203–226, vol. 4 (3).

W.G. Crewther, et al., "Reduction of S–Carboxymethylcysteine and Methionine with Sodium in Liquid Ammonia," Biochim. Biophys. Acta, (1969) pp. 609–611, vol. 164.

W.T. Agar, et al., "The Isolation from Wool of a Readily Extractable Protein of Low Sulphur Content," Biochim. Biophys Acta, (1958) pp. 225–226, vol. 27.

H. Lindley, et al., "The Reactivity of the Disulphide Bonds of Wool," Biochem J. (1974) pp. 515–523, vol. 139.

M. Schornig, et al., "Synthesis of Nerve Growth Fractor mRNA in Cultures of Developing Mouse Whisker Pad, A Peripheral Target Tissue of Sensory Trigeminal Neurons," The Journal of Cell Biology. (Mar. 1993) pp. 1471–1479. vol. 120. No. 6.

S. Mitsui, et al., "Genes for a Range of Growth Factors and Cyclin–Dependent Kinase Inhibitors are Expressed by Isolated Human Hair Follicles," British Journal of Dermatology (1997) pp. 693–698, vol. 137.

B.K. Filshie, et al., "The Fine Structure of alpha–Keratin," J. Mol. Biol. (1961) pp. 784–786, vol. 3.

R.D.B. Fraser, et al., "Structure of alpha–Kertain," Nature, (Feb. 28, 1959) pp. 592–594, vol. 183.

R.D.B. Fraser, et al. "Helical Models of Feather Keratin Structure," Nature, (Sep. 22, 1962) pp. 1167–1168, vol. 195.

B.K.Filshie, et al., "An Electron Microscope Study of the fine Structure of Feather Keratin," The Journal of Cell Biology (1962) pp. 1–12, vol. 13.

W.G. Crewther, et al., "Low–Sulfur Proteins from alpha–Keratins. Interrelationships between their Amino Acid Compositions, alpha–Helix Contents, and the Supercontraction of the Parent Keratin," Biopolymers (1966) pp. 905–916, vol. 4.

G.M. Bhatnagar, et al., "The Conformation of the High–Sulphur Proteins of Wool 1. The Preparation and Properties of a Water–Sulphur Metakeratin," Int. J. Protein Research I. (1969), pp. 199–212.

W.G. Crewther, et al., "The Preparation and Properties of a Helix–Rich Fraction Obtained by Partial Proteolysis of Low Sulphur S–Carboxymethlkerateine from Wool," (1967) The Journal of Biological Chemistry (Issue of Oct. 10), pp. 4310–4319, vol. 242, No. 19.

D.A.D. Parry, et al., "Structure of alpha –Keratin: Structural Implication of the Amino Acid Sequences of the Type 1 and 11 Chain Segments," J. Mol. Biol. (1977) pp. 449–454, vol. 113.

E. Suzuki, et al., "X–Ray Diffraction and Infrared Studies of an alpha –Helical Fragment from alpha –Keratin," J. MolL. Biol. (1973) pp. 275–278, vol. 73.

G.M. Bhatnagar, et al., "The Conformation of the High–Sulphur Proteins of Wool: II. Difference Spectra of Kerateine–B," Int. J. Research1, (1969) pp. 213–219.

Dean R. Hewish et al., "In Vitro Growth and Differentiation of Epithelial Cells Derived from Post–Embroyonic Hair Follicles," Aust. J. Biol. Sci., (1982) pp. 103–109, vol. 35.

A.M. Downes, et al., "A Study of the Proteins of the Wool Follicle," Aust. J. Biol. Sci., (1966) pp. 319–333, vol. 19.

G. E. Rogers, et al., "Keratin Protofilaments and Riobosomes from Hair Follicles," Nature, (Jan. 2, 1965), pp. 77–78, vol. 205.

P.M. Steinert, et al., "In Vitro Studies on the Synthesis of Guinea Pig Hair Keratin Proteins," Biochimica et Biophysica Acta, (1973) pp. 403–412, vol. 312.

G.E. Rogers, et al., "Some Observations on the Proteins of the Inner Root Sheath Cells of Hair Follicles," Biochimica et Biophysica Acta, (1958) pp. 33–43, vol. 29.

Leslie N. Jones, et al., "Studies of Developing Human Hair Shaft Cells in Vitro," The Journal of Investigative Dermatology., (Jan. 1988) pp. 58–64, vol. 90.

Trevor Jarman, et al., "Prospects of Novel Biomaterials Development," Online Publications, Pinner, Uk, Presented at Biotech '85 (Europe) (1985) pp. 505–512.

Akira Tachibana, et al., "Fabrication of Wool Keratins Sponge Scaffolds for Long–Term Cells Cultivation," Journal of Biotechnology, (2002) pp. 165–170, vol. 93.

J.M. Gillispie, et al., "Periodicity in High–sulphur Proteins from Wool," Nature, (Sep. 18, 1965) pp. 530–531, vol. 246.

Kiyoshi Yamauchi, "The Development of Keratin: Characteristics of Polymer Films," [Research Report]; pp. 1–12.

"Scattering to Structural Foams, Skin, Synthetic" Encylopedia of Polymer and Science and Engineering, (1989) pp. 335–345, vol. 15.

J.M. Gillespie, et al., "Proteins Rich in Glycine and Tyrosine from Keratins," Comp. Biochem. Physiol., (1972) pp. 723–734, vol. 41B.

R.D.B. Fraser, et al., "Tyrosine–Rich Proteins in Keratins," Comp. Biochem. Physiol., (1973) pp. 943–947, vol. 44B.

J.M. Gillespie, et al., "Relation Between the Tyrosine Content of Various Wools and their Content of a Class of Proteins Rich In Tyrosine and Glycine," Aust. J. Biol. Sci., (1971) pp. 1189–1197, vol. 24.

J.M. Gillespie, et al., "The Macroheterogeneity of Type I Tyrosine–rich Proteins of Merino Wool," Aust. J. Biol. Sci., (1974) pp. 617–627, vol. 27.

E.G. Bendit, et al., "The Probable Role and Location of High–Glycine–Tyrosine Proteins in the Structure of Keratins," Biopolymers, (1978) pp. 2743–2745, vol. 17.

Robert C. Marshall, et al. "High–sulphur Proteins from alpha–Keratins: 11.* Isolation and Partial Characterization of Purified Components from Mouse Hair," Aust. J. Biol. Sci. (1976) pp. 11–20, vol. 29.

Robert C. Marshall, et al. "High–Sulphur Proteins from alpha–Keratins: 1. Heterogeneity of the Proteins from Mouse Hair," Aust. J. Biol. Sci. (1976) pp. 1–10, vol. 29.

R. L. Darskus, et al. "The Possibility of Common Amino Acid Sequences in High–Sulphur Protein Fractions From Wool," Aust. J. Biol. Sci. (1969) pp. 1197–1204, vol. 22.

Robert C. Marshall, et al. "Heterogeneity and Incomplete Disulfide Reduction in the High–Sulfur Proteins of Wool," Aust. J. Biol. Sci. (1978) pp. 219–229, vol. 31.

H. Lindley, et al., "The Preparation and Properties of a Group of Proteins from the High– Sulphur Fraction of Wool," Biochem. J. (1972) pp. 859–867, vol. 128.

J.M. Gillespie, et al., "Evidence of Homology in a High–Sulphur Protein Fraction (SCMK–B2) of Wool and Hair alpha –Keratins," Biochem. J. (1968) pp. 193–198, vol. 110.

J.M. Gillespie, et al., "A Comparative Study of High–Sulphur Proteins from alpha–Keratins," Comp. Biochem. Physiol. (1965) pp. 175–185, vol. 15.

J.M. Gillespie, et al., "High–Sulphur Proteins as a Major Cause of Variation in Sulphur Content Between alpha –Keratins," Nature (Sep. 18, 1965) pp. 1293–1294, vol. 207.

R.D.B. Fraser, et al., "Molecular Organization in Alpha–Keratin," Nature, (Mar. 17, 1962) pp. 1052–1055, vol. 193.

DR. P. Alexander, et al., "Structure of Wool Fibres," Nature, (Sep. 2, 1950) pp. 396–398.

Node, et al., "Hard Acid and Soft Nucleophile System. 2. Demethylation of Methyl Ethers of Alcohol and Phenol with an Aluminum Halide–Thiol System," J. Org. Chem (1980), pp. 4275–4277, vol. 45.

Ito, et al., "Biocompatibility of Denatured Wool Keratin," Konbushi Ronbunshu [Collected Essays on Polymers], (Apr. 1982) pp. 249–256, vol. 39, No. 4.

Tatsuya and Ishii, "Keratin Protein High Pressure Molded Article,"; Japanese Patent Application, (Dec. 03, 1993), total of six pages, Public Patent Announcement 1993–320358.

Saeki, Yokogawa, and Uehara, "Production Method For Water–soluble Keratin Protein," Japanese Patent Application, (Feb. 21, 1990), total of five pages, Public Patent Announcement 1990–51533.

Miyamoto and Tsushima, "A Method for Preparing a Keratin Substance with a Low Molecular Weight," Japanese Patent Application, (Jul. 8, 1982), total of five pages; Public Patent Disclosure Bulletin S57–109797.

R.D.B. Fraser, "The Chain Configuration of Wool Keratin," Short Communications, Preliminary Notes, (1953) pp. 482–483, vol. 12.

R.D.B. Fraser, et al., "Microscopic Observations of the Alkaline–Thioglycollate Extraction of Wool," Short Communications, Preliminary Notes, (1953) pp. 484, vol. 12.

Van Dyke Mark et al., Development of keratin coatings for osteoinduction on titanium, ,Abstracts of Papers American Chemical Society, vol. 224, No. 1–2, Aug. 18–22, 2002.

Tanaka, Yoshio et al., Reaction of Wool Keratin with Epoxides, Proceedings International Wolltextil–Forschungskonf, vol. 3, 1976, pp. 192–201.

Fraenkel–Conrat, H., The Action of 1, 2–Epoxides on Proteins, Journal of Biological Chemistry, vol. 154, No. 1, Jun. 1, 1944.

Weetall HH.; Preparation of immobilized proteins covalently coupled through silane coupling agents to inorganic supports; Applied Biochemistry and Biotechnology; 1993; 157–188; 41(3).

Weetall, HH.; Preparation of immobilized proteins covalently coupled through silane coupling agents to inorganic supports; Advances in Molecular and Cell Biology; 1996; 161–192; 15A.

* cited by examiner

METHODS FOR PRODUCING, FILMS COMPRISING, AND METHODS FOR USING HETEROGENOUS CROSSLINKED PROTEIN NETWORKS

CROSS-REFERENCE TO RELATED APPLICATIONS

The present application is related to the following pending applications: U.S. patent application Ser. No. 10/133,885, filed Apr. 26, 2002; and U.S. patent application Ser. No. 10/127,523, filed Apr. 22, 2002. The present application is also related to the following provisional applications: U.S. Provisional Application 60/200,543, filed Apr. 27, 2000; U.S. Provisional Application 60/225,517, filed Aug. 15, 2000; U.S. Provisional Application 60/324,709, filed Sep. 25, 2001; U.S. Provisional Application 60/393,958, filed Jul. 5, 2002; and U.S. Provisional Application 60/399,039, filed Jul. 25, 2002.

FIELD OF THE INVENTION

The present invention is directed to methods for producing biocompatible heterogeneous proteinaceous networks crosslinked with a heterogeneous crosslinking agent. Preferred proteins for use in forming the networks are α-keratins, or high molecular weight keratins (HMWK's). The crosslinking agent preferably reacts with reactive pendant groups existing on the keratin molecules and either produces no byproducts, produces biocompatible byproducts, such as hydrogen, water, and carbon dioxide, or produces byproducts that can be removed from the network.

BACKGROUND OF THE INVENTION

Proteins, such as keratin proteins, are beneficial in healing damaged epithelial tissues. Unfortunately, the chemical and engineering properties of keratin proteins have been relatively limited to those achieved using oxidative and reductive chemistries, and side chain protein crosslinks. A need exists for proteins, and methods for crosslinking proteins, preferably α-keratins, to form films having a broad scope of chemical and engineering properties so that the potential applications of protein-based materials can be expanded.

SUMMARY OF THE INVENTION

A method is provided for producing functionalized proteins comprising reactive pendant groups effective to react with heterogeneous crosslinking agents and to form heterogeneous proteinaceous networks. The proteins are treated with a reactive nucleophile under conditions effective to convert thiol groups to thiolate anions. The thiolate anions are exposed to a functionalization agent comprising a substitution end and at least one reactive end under conditions effective to induce said thiolate anions to react with said substitution end, thereby producing a plurality of functionalized proteins comprising reactive pendant groups comprising said reactive end. In a preferred embodiment, the reactive end is an epoxide group, and the functionalized proteins are exposed to conditions effective to induce the epoxide groups to react with reactive amines pendant on the proteins, producing a heterogeneous cross-linked protein network. The protein preferably is selected from the group consisting of α-keratin, collagen, and elastin. The functionalization agent preferably is epichlorohydrin.

In another aspect, a method is provided comprising exposing said plurality of functionalized proteins, preferably functionalized α-keratins, to a crosslinking agent comprising at least a first terminus reactive toward said reactive end and a second terminus reactive toward an entity selected from the group consisting of said reactive end and other reactive pendant groups, said exposing occurring under conditions effective to induce said first terminus on a plurality of molecules of said crosslinking agent to react with said reactive end on a plurality of first functionalized α-keratin molecules, and to induce said second terminus on a plurality molecules of said crosslinking agent to react with said entity on a plurality of second functionalized α-keratin molecules, producing a cross-linked protein network. The reactive end preferably is selected from the group consisting of an an anhydride group, a carboxylic acid group, an epoxide group, and an isocyanate group. The proteins are selected from the group consisting of keratin, collagen, and elastin, most preferably α-keratin.

A method is provided for making a keratin network comprising a heterogeneous crosslinking agent, said method comprising exposing α-keratins comprising reactive pendant groups to a heterogeneous crosslinking agent comprising a first functional group and a second functional group adapted to react with said reactive pendant groups under conditions effective to induce a first reaction between said first functional groups on a plurality of molecules of said crosslinking agent and first reactive pendant groups on a plurality of first α-keratin molecules and to induce a second reaction between said second functional groups on a plurality of molecules of said crosslinking agent and second reactive pendant groups on a plurality of second α-keratin molecules, thereby producing a heterogeneous cross-linked keratin network In one aspect, the method comprises exposing α-keratins comprising reactive pendant groups to a nucleophilic substitution agent comprising a substitution end and at least one terminal epoxide under conditions effective to induce said reactive pendant groups to react with said substitution end, thereby producing a plurality of epoxidized α-keratins comprising epoxidized pendant groups. The reactive pendant groups preferably are thiolate anions, and the functionalization agent preferably is epichlorohydrin. In another aspect, the method further comprises treating said plurality of epoxidized α-keratins with a multi-functional crosslinking agent comprising at least a first nucleophilic group and a second nucleophilic group under conditions effective to induce first epoxidized pendant groups on a plurality of first epoxidized α-keratin molecules to react with said first nucleophilic group on a plurality of molecules of said crosslinking agent, and to induce said second epoxidized pendant groups on a plurality of second epoxidized α-keratin molecules to react with said second nucleophilic group on a plurality of molecules of said crosslinking agent, producing said cross-linked α-keratin network.

In another aspect, the method comprises exposing α-keratins comprising reactive pendant groups to a crosslinking agent comprising at least a first terminal epoxide and a second terminal epoxide under conditions effective to induce a first reaction between said first terminal epoxides on a plurality of molecules of said crosslinking agent and first reactive pendant groups on a plurality of first α-keratin molecules, and to induce a second reaction between said second terminal epoxides on a plurality of molecules of said crosslinking agent and second reactive pendant groups on a plurality of second α-keratin molecules, thereby producing a heterogeneous cross-linked keratin network. In a preferred embodiment, said reactive pendant groups are selected from the group consisting of thiol groups and reactive amines.

In another aspect, the method comprises exposing α-keratins comprising reactive pendant groups to a crosslinking agent comprising at least a first functionality and a second functionality independently selected from the group consisting of an ester group and a carboxylic acid group under conditions effective to induce first reactions between said first functionality on a plurality of molecules of said crosslinking agent and first reactive pendant groups on a plurality of first α-keratin molecules, and to induce second reactions between said second functionality on a plurality of molecules of said crosslinking agent and second reactive pendant groups on a plurality of second α-keratin molecules, thereby producing a heterogeneous cross-linked keratin network. Preferred crosslinking agents include, but are not necessarily limited to anhydrides and dicarboxylic acids. More preferred crosslinking agents are phthallic anhydride and terepthalic acid. Preferred reactive pendant groups are selected from the group consisting of thiols, hydroxyls, and reactive amines, preferably thiols.

In yet another aspect, the method comprises exposing α-keratins comprising reactive pendant groups to a crosslinking agent comprising at least a first isocyanate group and a second isocyanate group under conditions effective to induce a first reaction between said first isocyanate groups on a plurality molecules of said crosslinking agent and first reactive pendant groups on a plurality of first α-keratin molecules, and to induce a second reaction between said second isocyanate groups on a plurality of molecules of said crosslinking agent and said second reactive pendant groups on a plurality of second α-keratin molecules, thereby producing a heterogeneous cross-linked keratin network. The crosslinking agent preferably is a diisocyanate selected from the group consisting of aryl diisocyanates, including benzyl diisocyanate, alkyl diisocyanates, and allyl diisocyanates having from about 1 to about 8 carbon atoms. A preferred diisocyanate is hexanediisocyanate. Reactive pendant groups preferably are selected from the group consisting of hydroxyl groups, thiol groups, and reactive amine groups.

In another aspect, the method comprises exposing proteins comprising reactive pendant groups to a heterogeneous crosslinking agent comprising a first functional group and a second functional group adapted to react with said reactive pendant groups under conditions effective to induce a first reaction between said first functional groups on a plurality of molecules of said crosslinking agent and first reactive pendant groups on a plurality of first protein molecules, and to induce a second reaction between said second functional groups on a plurality of molecules of said crosslinking agent and second reactive pendant groups on a plurality of second soluble protein molecules, thereby producing a heterogeneous cross-linked proteinaceous network. The proteins are selected from the group consisting of keratin, collagen, and elastin, most preferably α-keratin.

In another embodiment, a heterogeneous crosslinked protein network is provided comprising a plurality of protein molecules interlinked by at least one crosslinking agent, said network comprising first bonds between first functional groups on a plurality of molecules of said crosslinking agent and first reactive pendant groups on a plurality of first protein molecules and second bonds between second functional groups on a plurality of molecules of said crosslinking agent and second reactive pendant groups on a plurality of second protein molecules. The protein molecules suitably are selected from the group consisting of keratin, collagen, and elastin, most preferably α-keratin. In a preferred embodiment, the crosslinking agent is heterogeneous and comprises a plurality of said functional groups. Suitable functional groups are selected from the group consisting of alkoxide groups, vinyl groups, hydroxyl groups, amine groups, aldehyde groups, isocyanate groups, ester groups, and anhydride groups. Preferred alkoxides are epoxides.

In a preferred embodiment, the heterogeneous crosslinked keratin network comprises a plurality of α-keratin molecules interlinked by a crosslinking agent, said network comprising first bonds between first functional groups on a plurality of molecules of said crosslinking agent and first pendant groups on a plurality of first α-keratin molecules and second bonds between second functional groups on a plurality of molecules of said crosslinking agent and second reactive pendant groups on a plurality of second α-keratin molecules. In a most preferred embodiment, the first bonds and the second bonds are covalent bonds. Suitable functional groups are selected from the group consisting of alkoxide groups, vinyl groups, hydroxyl groups, amine groups, aldehyde groups, isocyanate groups, ester groups, and anhydride groups. Preferred reactive pendant groups are selected from the group consisting of hydroxyl groups, thiol groups, reactive amine groups, and alkoxides. Preferred alkoxides are epoxides.

In a preferred embodiment, the heterogeneous crosslinked network comprises the following crosslinks:

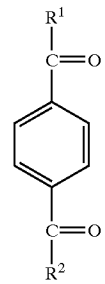

wherein $R^1$ and $R^2$ independently are amino acid residues from separate protein molecules, the residues being selected from the group consisting of cysteine, arginine, serine, lysine, asparagine, glutamine, tyrosine, tryptophan, and histidine. Preferably, $R^1$ and $R^2$ independently are selected from the group consisting of cysteine and arginine. In a most preferred embodiment, $R^1$ and $R^2$ are cysteine, as shown below:

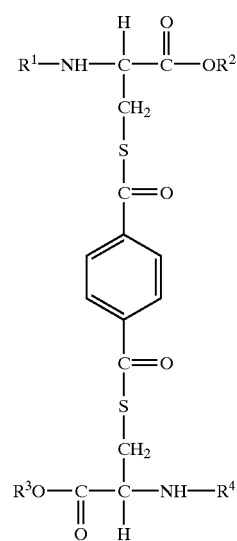

In another preferred embodiment, the heterogeneous crosslinked network comprises the following crosslinks:

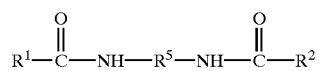

wherein $R^1$ and $R^2$ independently are amino acid residues from separate protein molecules, the residues being selected from the group consisting of cysteine, arginine, serine, lysine, asparagine, glutamine, tyrosine, tryptophan, and histidine; and, $R^5$ is selected from the group consisting of alkoxy groups, alkylene groups, and alkenyl groups having from about 1 to about 50 carbon atoms, alone, or in combination with cyclic alkyl groups or aromatic groups. Preferably, $R^1$ and $R^2$ independently are selected from the group consisting of glutamic acid and aspartic acid.

In another preferred embodiment, the heterogeneous crosslinked network comprises the following crosslinks, wherein $R^1$ and $R^2$ are the remainder of a first protein molecule and $R^3$ and $R^4$ are the remainder of a second protein molecule:

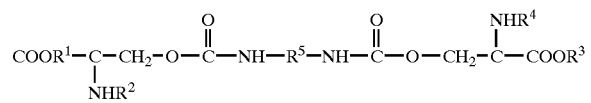

In another preferred embodiment, the heterogeneous crosslinked network comprises the following crosslinks, wherein $R^1$ and $R^2$ are the remainder of a first protein molecule and $R^3$ and $R^4$ are the remainder of a second protein molecule:

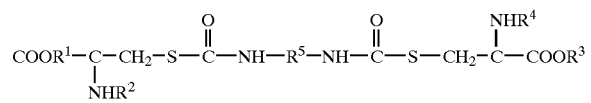

In another preferred embodiment, the heterogeneous crosslinked network comprises the following crosslinks, wherein $R^1$ and $R^2$ are the remainder of a first protein molecule and $R^3$ and $R^4$ are the remainder of a second protein molecule:

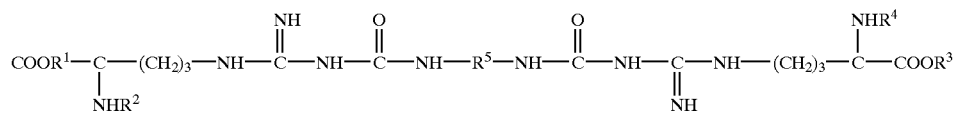

In another preferred embodiment, the heterogeneous crosslinked network comprises the following crosslinks:

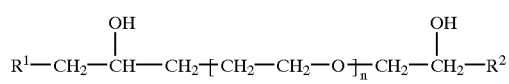

wherein: n is from about 1 to about 50; and, $R^1$ and $R^2$ independently are amino acid residues from separate protein molecules, the residues being selected from the group consisting of cysteine, arginine, serine, lysine, asparagine, glutamine, tyrosine, tryptophan, and histidine. Preferably, $R^1$ and $R^2$ independently are selected from the group consisting of cysteine and arginine. In a preferred aspect of this embodiment, $R^1$ and $R^2$ are cysteine. In a most preferred embodiment, $R^1$ and $R^2$ are cysteine residues and n is 1. The structure is shown below:

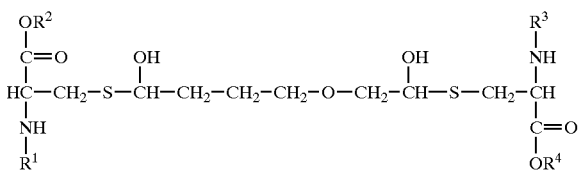

In another preferred embodiment, the heterogeneous crosslinked network comprises the following crosslinks, wherein $R^1$ and $R^2$ are the remainder of a first protein molecule and $R^3$ and $R^4$ are the remainder of a second protein molecule:

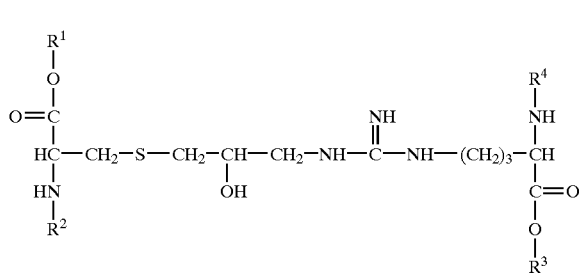

Another preferred aspect is a film made using any of the foregoing processes, or comprising any of the foregoing crosslinks.

DETAILED DESCRIPTION OF THE INVENTION

The present invention is directed toward methods for crosslinking proteins, preferably using heterogeneous crosslinking agents to form heterogeneous proteinaceous networks or films. As used herein, the term "heterogeneous" refers to a proteinaceous network or film, preferably comprising protein molecules having a relatively high molecular weight of from about 50 to about 85 kDa, or derivatives therefrom. The protein molecules are interlinked by a non-proteinaceous crosslinking material.

The methods described herein may be used to treat a wide variety of proteins to form network structures, preferably elastomeric films. Examples of suitable naturally occurring proteins include, but are not necessarily limited to keratin, collagen, and elastin. The proteins may be natural, synthetic, or recombinant. Preferred proteins are relatively high in cysteine content. Most preferred proteins are keratin proteins, even more preferably α-keratin proteins, also sometimes called high molecular weight keratins (HMWK's).

A preferred source of keratin proteins is hair or fur. The hair may be animal, or human. Keratins are loosely defined as the hardened and insolubilized proteins found in the epidermal cells of vertebrates. Human hair is composed almost entirely of keratins.

Human hair has a cuticle, which is a tough tubular outer layer made up of flattened cells arranged in a scaly, overlapping profile. The inner bulk of the hair is called the cortex and is constructed from elongated cells that are densely packed with fibrous keratins. The fibrous keratins are arranged in bundles referred to as microfibrils and possess an α-helical tertiary structure. The microfibrils are bound together with an amorphous keratin matrix.

The amorphous keratin matrix and the microfibrils vary in function and composition. The matrix is the "glue" that holds the microfibrils together. This matrix "glue" is high in sulfur content, and is comprised of low molecular weight keratins (LMWK) which typically have an average molecular weight of from about 10 to about 15 kDa. The microfibrils are comprised of high molecular weight keratins (HMWK) having a relatively lower sulfur content, but having a higher average molecular weight of typically from about 50 to about 85 kDa. HMWK's and LMWK's vary in chemical properties, such as reactivity and solubility.

Keratins are afforded their structural integrity, in large part, by the presence of disulfide crosslinks which form a three dimensional network of polypeptide chains. This network structure renders keratins insoluble. Keratins can, however, be made water soluble by destroying this three dimensional structure via disulfide bond scission. Disulfide bond scission can be performed either oxidatively, reductively, or using some combination of both types of bond scission. Oxidative bond scission with hydrogen peroxide, for example, results in the formation of sulfonic acid residues produced from cystine. The material produced using hydrogen peroxide for disulfide bond scission is highly ionic and has excellent water solubility. Reductive bond scission with mercaptoethanol, for example, results in the formation of cysteine residues produced from cystine. The material produced using this reductive technique is highly reactive and will readily re-crosslink.

Disulfide Bond Scission and Keratin Extraction

The proteins, preferably α-keratins, may be processed and/or isolated in any manner that renders them sufficiently soluble in the reaction media for crosslinking reaction(s) to occur. A number of the reactions described below call for an anhydrous solvent. Persons of ordinary skill in the art will recognize that anhydrous solvents include a large number of solvents, including, but not necessarily limited to 1,2,-dimethoxyethane, dimethylformamide, dimethylsulfoxide (DMSO), N-methyl pyrrolidone, and others. Generally, the reactions require the presence of at least some water.

Oxidation/Reduction of Cystine Residues

In a preferred embodiment, which uses keratins as a source material (e.g. human hair), the hair is oxidized by a suitable oxidizing agent. Suitable oxidizing agents include, but are not necessarily limited to hydrogen peroxide, peracetic acid, percarbonates, persulfates, chlorine dioxide, sodium and calcium peroxides, perborates, and hypochlorite. The oxidants are used at a concentration of up to about 35%, preferably at from about 0.1% to about 10%. The oxidation preferably occurs at reflux temperatures.

In a preferred embodiment, the hair is treated with hydrogen peroxide ($H_2O_2$), at from about 0.1% to about 10%, most preferably 1%, in order to disrupt the cuticle and swell the keratin source material. This process also converts some fraction of the cystine residues into sulfonic acid groups. The amount of oxidation may be controlled by varying the time of oxidation, preferably from about 0 hours to about 4 hours, while retaining the other conditions of the oxidation reaction constant. These conditions include concentration and type of oxidant, temperature, and ratio of extracting media to keratin source material. After the reaction is complete, the oxidized hair is filtered and rinsed, preferably with deionized water. The filtrate is discarded and the hair allowed to dry.

Where other conditions of oxidation are maintained constant, the conversion rate of cystine to sulfonic acid residues is roughly proportional to the amount of time used for the oxidation. Residual cystines in the resulting oxidized keratin solids are converted to other sulfur-containing moieties using reductive techniques. Preferably, the disulfide-bridged cystine group is converted to a thiol group, which has utility of it's own, or can be modified using a variety of chemical techniques.

Reaction with a Reducing Agent

If oxidized, the oxidized hair preferably is treated with a reducing agent. Treatment of oxidized keratin proteins with reducing agents facilitates the formation of cysteine from cystine, but tends to leave the previously oxidized groups unaltered. Suitable reducing agents include, but are not necessarily limited to thioglycolic acid and salts thereof, mercaptoethanol, dithiothreitol, thioglycerol, thiolactic acid, glutathione, cysteine, sodium sulfide, and sodium hydrosulfide. Preferred reducing agents are thioglycolic acid and mercaptoethanol, most preferably thioglycolic acid.

In order to treat the oxidized hair with the reducing agent, the previously oxidized hair is suspended in the reducing agent typically at a concentration of up to about 10N, preferably from about 0.1N and 1N; at a pH greater than about 7, preferably equal to or greater than 9, most preferably 9; a temperature of from about 25 to about 80° C., preferably about 60° C., preferably for a time period of from about 1 to about 72, most preferably about 24 hours. The reaction occurs under an inert atmosphere, preferably nitrogen. The liquid fraction is separated from any remaining solids using known means, including but not necessarily limited to filtration, or cannulation and/or centrifugation, preferably under inert atmosphere. A preferred method of separation is filtration. Once the solids are removed, the soluble keratin proteins are isolated from the solution by addition of a water-miscible non-solvent, or by spray drying. Water-miscible non-solvents include, but are not necessarily limited to ethanol, methanol, isopropyl alcohol, tetrahydrofuran, acetone, dioxane, and the like, again under inert atmosphere. A preferred non-solvent is ethanol. The precipitate is separated from the non-solvent using known means, preferably by filtration and rinsing using additional aliquots of the non-solvent. The resulting keratin proteins are dried using known techniques, preferably overnight under vacuum at room temperature. This process results in the keratins having both sulfonic acid groups and thiol groups.

Thiols possess reactivities similar to alcohols, and can be used to perform a multitude of known organic chemical reactions, such as those described in McMurry, J., *Organic Chemistry*, Brooks/Cole Publishing Co., Monterey, Calif. (1984); Scudder, P. H., Electron Flow in Organic Chemistry, John Wiley & Sons, New York, N.Y. (1992); Stowell, J. C., *Intermediate Organic Chemistry*, John Wiley & Sons, New York, N.Y. (1994), incorporated herein by reference. The ratio of sulfonic acid to thiol is primarily controlled by the quantity of primary reactive sites remaining after oxidation. Of course, the rate of reduction will also be affected by reagent concentration(s), reaction temperature(s), and exposure time(s).

Reductive/Reductive Extraction

Reductive chemistries also are known for disulfide bond scission in keratins: See Wardell, J. L., "Preparation of Thiols" in *The Chemistry of the Thiol Group*, Patai, S. (Editor), pp. 163–353, John Wiley & Sons, New York, N.Y. (1974), incorporated herein by reference. HMWK's may be extracted from hair using at least two reductive extractions, as described in Crewther, W. G., Fraser, R. D. B., Lennox, F. G., and Lindley, H., "The Chemistry of Keratins" in *Advances in Protein Chemistry*, Anfinsen, C. B., Jr., Anson, M. L., Edsall, J. T., and Richards, F. M. (Editors), Academic Press, New York, pp. 191–346 (1965), incorporated herein by reference.

Briefly, in a first reductive extraction, the hair is treated with a first reducing agent under first conditions effective to selectively extract matrix keratins, producing a first solution comprising soluble reduced matrix keratins and remaining hair solids. The remaining hair solids and the first solution are separated, and the remaining hair solids are exposed to a second extraction solution under second conditions effective to solubilize α-keratins, producing a second solution comprising soluble reduced α-keratins and solid cuticle. Once the second extraction is complete, the remaining solids essentially are the empty, intact cuticle.

The liquid fraction is separated from the solid cuticle using known means, including but not necessarily limited to filtration, or cannulation and/or centrifugation, preferably under inert atmosphere. A preferred method of separation is filtration. Once the solids are removed, the soluble keratin proteins are isolated from the solution by addition of a water-miscible non-solvent, or by spray drying. Water-miscible non-solvents include, but are not necessarily limited to ethanol, methanol, isopropyl alcohol, tetrahydrofuran, acetone, dioxane, and the like, again under inert atmosphere. A preferred non-solvent is ethanol. The precipitate is separated from the non-solvent using known means, preferably by filtration and rinsing using additional aliquots of the non-solvent. The resulting keratin proteins are dried using known techniques, preferably overnight under vacuum at room temperature. The dried keratin proteins are ground into a powder, sometimes referred to as "HMWK powder."

Network Formation

Thiols and other chemical moieties contained in amino acid residues have utility as labile sites for crosslinking reactions to form protein networks, preferably networks having the properties of an elastomeric film. Preferred reactions and crosslinking agents are those which produce biocompatible byproducts, preferably hydrogen, water, carbon dioxide, or any other biocompatible byproduct that is readily metabolized or excreted, removed from the network, or at least is not toxic to the human body. In order to prepare the networks, the desired crosslinking agent(s) are determined. Crosslinking agents having either two or more of the same functional groups, or two or more different functional groups are suitable. Preferable crosslinking agents have two or more of the same functional group, as described below.

In a preferred embodiment, which uses HMWK proteins, the HMWK proteins are dissolved in an aqueous solvent. Preferably, about 2 g of HMWK powder is mixed in water containing a suitable base, and the mixture is stirred and heated to a temperature effective to dissolve the keratin, typically not more than 60° C. The pH of the solution is maintained at about 9 to 11 using a suitable base. Suitable bases include, but are not necessarily limited to ammonium hydroxide, sodium hydroxide, and potassium hydroxide, preferably ammonium hydroxide. At least about 5 wt. %, preferably about 10 wt. %, relative to the keratin, of a multifunctional crosslinking agent is added to the mixture, forming a network precursor solution. Depending upon the crosslinking agent, a catalyst or promotor may be added. The network precursor solution is distributed over an appropriate surface or mold, preferably to a thickness of from about 1 to about 10 mm, and cured by exposure to suitable energy, such as a heat lamp, an autoclave, a microwave, or a UV lamp. In a preferred embodiment, the solutions are placed under a heat lamp effective to produce a temperature of at least about 60° C. for from about 30 to 300 minutes.

Crosslinking Reactions

Crosslinking of the proteins and network formation occurs, generally, when a non-protein reactant which is at least difunctional, or has at least two reactive groups, is used to crosslink between reactive pendant groups on two different keratin molecules. The non-protein reactant creates a bridge between keratin molecules, and thus produces a three-dimensional network.

Proteins comprise amino acids, which generally have the formula:

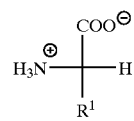

Table 1 summarizes the amino acid residues found in human hair, for example, and shows the "$R^1$" groups associated with each residue.

TABLE 1

Ranked average amounts of amino acids in human hair

| Amino Acid | $R^1$ Group | Nature | pKa | Iso-electric Point (pH) | Percent Composition in Hair |
|---|---|---|---|---|---|
| Cysteine | H—S—CH$_2$— | Nonpolar | 8.4 | 5.02 | 17.3 |
| Glutamic Acid | HO—C(=O)—CH$_2$—CH$_2$— | Polar | 4.5 | 3.22 | 13.9 |
| Arginine | NH$_2$—C(=NH)—N(H)—(CH$_2$)$_3$— | Polar | 12.5 | 11.15 | 9.85 |
| Serine | HO—CH$_2$— | Polar | None | 5.68 | 9 |

TABLE 1-continued

Ranked average amounts of amino acids in human hair

| Amino Acid | R¹ Group | Nature | pKa | Iso-electric Point (pH) | Percent Composition in Hair |
|---|---|---|---|---|---|
| Threonine | CH₃—CH(OH)— | Polar | None | 5.64 | 7.75 |
| Leucine | (CH₃)₂CH—CH₂— | Hydrophobic | None | 5.98 | 7.35 |
| Proline | (pyrrolidine ring) | Hydrophobic | None | 6.3 | 6.95 |
| Aspartic Acid | HO—C(=O)—CH₂— | Polar | 4.5 | 2.77 | 5.8 |
| Valine | (CH₃)₂CH— | Hydrophobic | None | 5.96 | 5.7 |
| Isoleucine | CH₃—CH₂—CH(CH₃)— | Hydrophobic | None | 5.94 | 4.75 |
| Glycine | H— | Nonpolar | None | 5.65 | 4.15 |
| Phenylalanine | C₆H₅—CH₂— | Hydrophobic | None | 5.48 | 3 |
| Alanine | CH₃— | Hydrophobic | None | 6 | 2.8 |
| Tyrosine | HO—C₆H₄—CH₂— | Hydrophobic | None | 5.66 | 2.6 |
| Lysine | NH₂—(CH₂)₄— | Polar | 10.4 | 9.59 | 2.5 |
| Histidine | (imidazole)—CH₂— | Aromatic | 6.2 | 7.47 | 0.9 |
| Methionine | CH₃—S—CH₂—CH₂— | Hydrophobic | None | 5.74 | 0.85 |
| Tryptophan | (indole)—CH₂— | Hydrophobic | None | 5.89 | 0.85 |

The most abundant amino acid in human hair is cysteine, which is found in the form of disulfide-bridged cystine groups. As discussed above, this group can be converted to other sulfur containing moieties, most notably thiol. Thiols theoretically can be reacted with reactive ends of a crosslinking agent using a number of chemical techniques, such as those described in S. Patai (Ed.), *the Chemistry of the Thiol Group*, Parts 1 and 2, John Wiley & Sons, New York, N.Y. (1974), incorporated herein by reference. Other reaction scenarios, such as those directed toward polymer synthesis, also are useful to convert thiols to an assortment of desirable functional residues, including those described in Rempp, P. and Merrill, E. W., *Polymer Synthesis*, Huethig & Wepf Verlag Basel, Heidelberg, Germany (1986); Young, R. J. and Lovell, P. A., *Introduction to Polymers*, Chapman & Hall, London (1991); Odian, G., *Principles of Polymerization*, John Wiley & Sons, New York, N.Y. (1991), incorporated herein by reference.

In addition to cysteine, the following amino acids have pendant groups comprising nitrogen or oxygen which may be useful as reactive pendant groups; arginine, serine, glutamic acid, threonine, aspartic acid, lysine, asparagine, glutamine, tyrosine, tryptophan, and histidine. Where the protein is α-keratin, preferred amino acid residues comprising reactive pendant groups for crosslinking are cysteine, arginine, serine, and glutamic acid, most preferably cysteine and arginine.

Crosslinking agents comprise at least one reactive group, preferably at least two reactive groups. Preferred reactive groups are selected from the group consisting of epoxide groups, isocyanate groups, and carboxyl groups. Most preferred crosslinking agents are diepoxides, diisocyanates, and dicarboxylates, including anhydrides and hydrolyzed diacids thereof. For convenience, the crosslinking agents described herein sometimes are referred to as "di-" functional. However, unless a crosslinking agent is expressly claimed or expressly stated to be di-functional only, it is to be understood that the crosslinking agents described herein may also be multi-functional, e.g., di-, tri, tetra-, etc. The non-functional portion of the molecule ($R^5$, below) generally forms the remainder of the "bridge" crosslinking the protein molecules. $R^5$ is biocompatible and typically is an organic moiety. Suitable organic moieties include, but are not necessarily limited to alkoxy groups, alkylene groups, and alkenyl groups having from about 1 to about 50 carbon atoms. The alkoxy groups, alkylene groups, or alkenyl groups may be present alone, or in combination with cyclic alkyl groups or aromatic groups.

Without limiting the invention to a particular theory or mechanism of action, unless expressly claimed, the following are crosslinking chemistries involved in producing the heterogeneous crosslinked protein networks:

Production of Thioether

A preferred reductive modification is the formation of a thiolate anion, followed by nucleophilic substitution employing an appropriate leaving group, yielding a thioether, preferably an alkoxy functional thioether (or a thioester). A preferred alkoxy functional thioether is an epoxy-functional thioether. The general reaction is shown below:

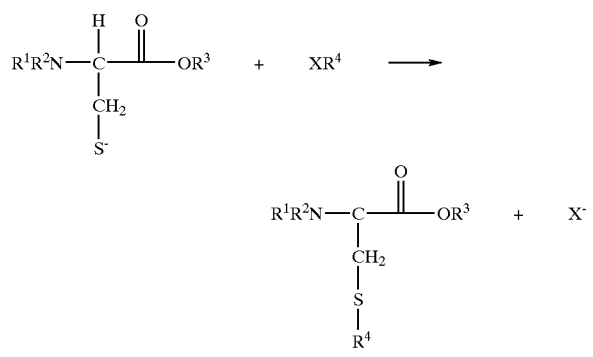

wherein $R^1$ and $R^2$ comprise entities selected from the group consisting of hydrogen and the remainder of the N-terminal portion of the protein molecule; $R^3$ comprises the remainder of the carboxy-terminal portion of the protein molecule; and, $R^4$ is a group adapted to form a thioether, preferably an alkoxy functional thioether. Suitable $R^4$ groups comprise a "substitution end," which bonds with the sulfur and a "reactive end" which reacts with the crosslinking agent. Suitable substitution ends include, but are not necessarily limited to unsubstituted and halo-substituted alkyl groups and alkylene groups having from about 1 to about 8 carbon atoms, including resonance hybrids, such as allyl groups, and unsubstituted and halo-substituted aryl groups. Suitable reactive ends include, but are not necessarily limited to acyl groups, and polyalkylethers containing from about 1 to 50 repeat groups, isocyanate groups, silane groups, and silicone groups. Preferred reactive ends include, but are not necessarily limited to carboxyl groups, isocyanate groups, and alkoxide groups. A most preferred reactive end is an epoxide group. In the foregoing formula, X may be any appropriate leaving group. Suitable leaving groups include, but are not necessarily limited to halide groups, tosylate groups, acetate groups, hydroxyl groups, alkoxy groups, and amine groups. Preferred X groups are halides, most preferably chlorine. In a most preferred embodiment, $XR^4$ is epichlorohydrin.

The thiolate anion can be generated from thiol, or more directly from the water soluble peptide feedstock, preferably a keratin feedstock, by reaction with a reactive nucleophile. Suitable nucleophiles include alkyl and aryl functional sulfide salts, sulfonates, isocyanates, thiocyanates, halides, hydrosulfide, hydroxide, alkoxides, azides, and acetates preferably alkyl and aryl sulfide salts, hydrosulfide, hydroxide, alkoxides, azides, and acetates.

The reaction where RX is epichlorohydrin is shown below:

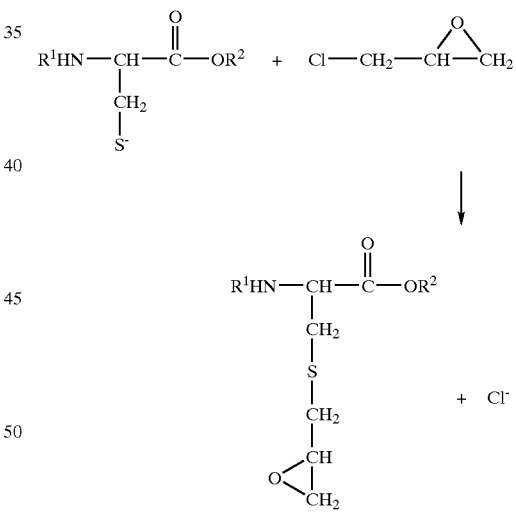

wherein $R^1$ and $R^2$ are the remainder of the water soluble peptide molecule of which cysteine is a part.

In order to form the foregoing epoxide functionalized water soluble peptides, preferably water soluble keratins, a water soluble keratin source material is first produced, preferably as described above. The water soluble keratins are then exposed to a solution of "RX", preferably epichlorohydrin, in aqueous solution at a pH of from about 9 to about 11. The RX is typically at a concentration of up to about 20 mole percent relative to keratin, preferably from about 5 to 10 mole percent relative to keratin, most preferably about 10 mole. %. The pH is greater than about 7, preferably greater than 9. The temperature is from about 20 to about 100° C., preferably about 60° C. The reaction continues for a time period of from about 1 to about 72 hours, most preferably about 24 hours. The result is epoxidized thiol groups.

The resulting epoxy functional thioether is reacted with a reactive pendant group on a second water soluble keratin peptide, including but not necessarily limited to a thiol group and a reactive nitrogen-containing group, such as an amine group. The following is an illustration of a crosslinking reaction between an epoxy functional thioether on one water soluble peptide and an arginine residue on another water soluble peptide:

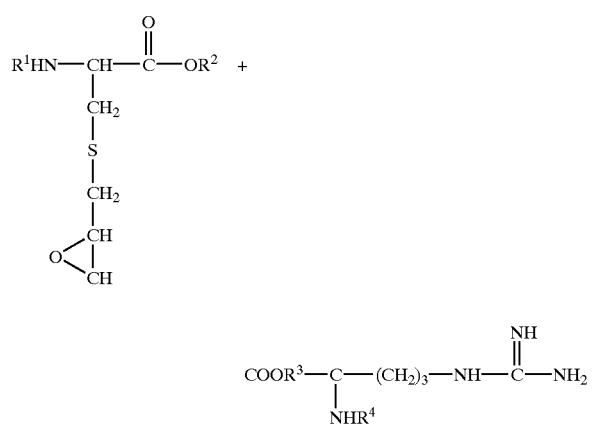

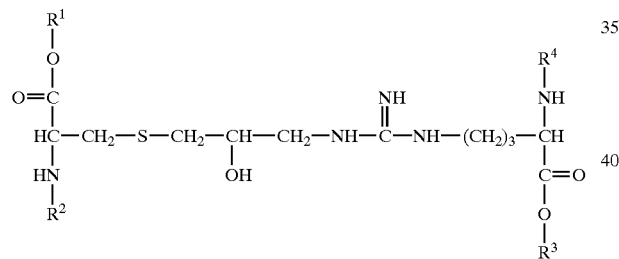

Peptide A                                              Peptide B $R^1$ and $R^2$ are the remainder of the water soluble peptide "A" bearing the epoxy functionalized cysteine, and $R^3$ and $R^4$ are the remainder of the water soluble peptide molecule B, containing the arginine residue. Although it is theoretically possible for water soluble peptide molecule A and B to be the same molecule, it is preferred for peptides A and B to be different molecules, preferably different water soluble α-keratin molecules.

Conversion of Thiol by Condensation

Condensation reactions such as transesterification, for example, can be used to generate thioesters. An example of a transesterification reaction is shown in Scheme 3.

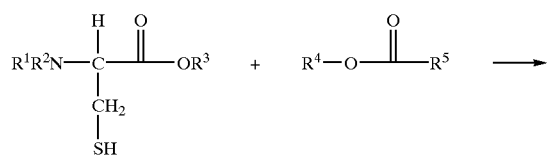

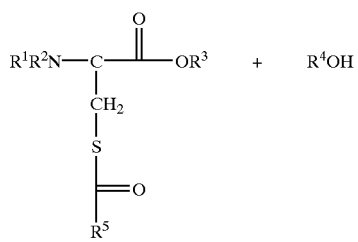

wherein $R^1$ and $R^2$ comprise entities selected from the group consisting of hydrogen and the remainder of the N-terminal portion of the protein molecule; $R^3$ comprises the remainder of the carboxy-terminal portion of the protein molecule; $R^4$ is an appropriate leaving group; and, $R^5$ is a functional hydrocarbon. Suitable $R^4$ groups include, but are not necessarily limited to hydrogen, alkyl groups having from about 1 to 6 carbon atoms, and aryl groups, including benzyl groups. Suitable $R^5$ groups include, but are not necessarily limited to aryl groups, including benzyl groups, and alkyl and allyl groups having from about 1 to about 20 carbon atoms in combination with any number of heteroatoms, such as oxygen and nitrogen, and polyalkylethers comprising from about 1 to 50 repeat groups.

Addition of Isocyanate to Hydroxyl Groups

In another preferred embodiment, a diisocyanate is reacted with hydroxyl groups in the keratin, such as those contained in serine. The reaction is shown below:

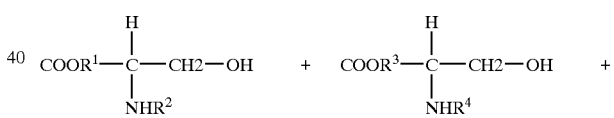

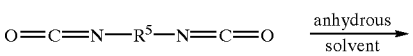

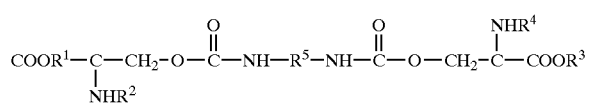

wherein $R^1$ and $R^2$ represent the remainder of one protein molecule, and $R^3$ and $R^4$ represent the remainder of a second protein molecule preferably a different α-keratin molecule. $R^5$ may be a variety of organic moieties effective to produce films having the desired properties. In a preferred embodiment, $R^5$ is selected from the group consisting of aryl groups, including benzyl groups, and alkyl and allyl groups having from about 1 to about 8 carbon atoms. In a preferred embodiment, $R^5$ is an alkyl group having 6 carbon atoms.

A similar reaction occurs with arginine:

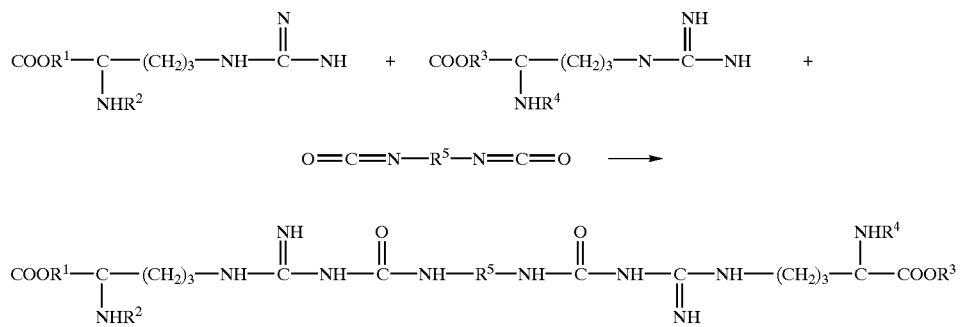

A similar reaction occurs with cysteine, as follows:

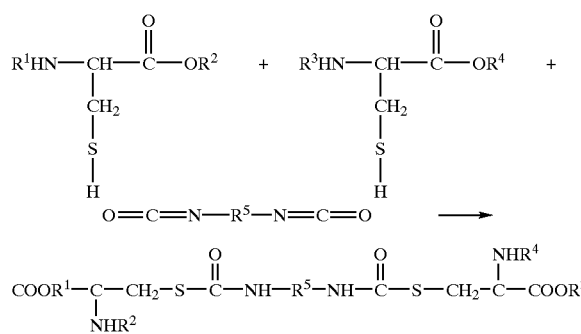

In order to perform these reactions, α-keratin proteins are dissolved in a suitable anhydrous solvent. Preferably, about 2 g of HMWK powder is mixed in an aprotic solvent containing a suitable base, preferably KOH, and the mixture is stirred and heated to a temperature effective to dissolve the keratin, typically about 75° C. Suitable aprotic solvents include, but are not necessarily limited to isopropyl alcohol, methyl sulfoxide, or DMF.

The resulting solutions are exposed to the isocyanate-containing reagent, including but not limited to aryl diisocyanates, including benzyl diisocyanate, and alkyl and allyl diisocyanates having from about 1 to 8 carbon atoms. A preferred diisocyanate is hexanediisocyanate. The solutions comprise an aprotic solvent and in the presence of an appropriate metal catalyst, preferably an organotin compound, most preferably dibutyltin dilaurate. The concentration of diisocyanate is about 20 mole percent relative to keratin dissolved in the same aprotic solvent, preferably between 5 and 10 mole percent relative to keratin, most preferably about 10%; at a temperature of from about 0 to about 100° C., preferably about 60–75° C., preferably for a time period of from about 0 to about 72 hours, most preferably about 24 hours or less, most preferably about 6 hours or less. The result is an elastomer which does not hydrolyze upon exposure to an aqueous buffer having a pH of about 7 for at least about 2 days, preferably at least about 7 days.

Addition of Amine Groups

Addition reactions between reactive amine groups and oxirane compounds occur readily without the aid of a catalyst. The crosslinking reaction with arginine is as follows:

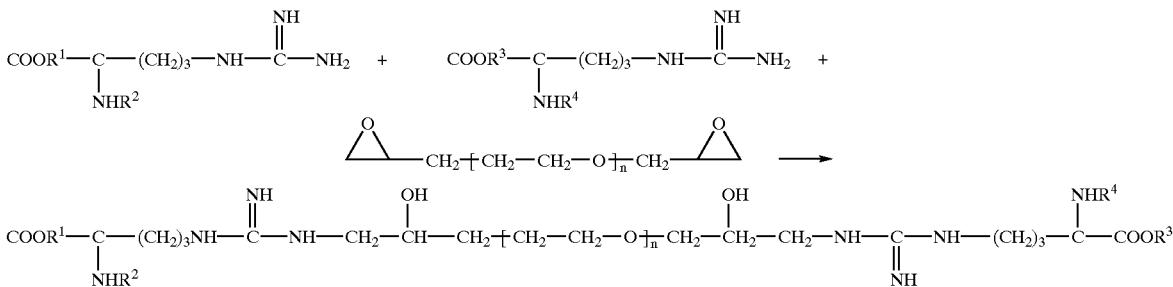

wherein $R^1$ and $R^2$ represent the remainder of one protein molecule and $R^3$ and $R^4$ represent the remainder of a separate protein molecule, preferably different α-keratin molecules.

In order to perform this reaction, solubilized keratins are exposed to a solution containing an oxirane-containing aliphatic or aromatic compound, typically at a concentration of up to about 20 mole percent relative to keratin, preferably between 5 and 10 mole percent relative to keratin; at a pH greater than 7, preferably greater than 9, or less than 7, preferably less than 6; at a temperature of from about 0 to about 100° C., preferably about 30° C., preferably for a time period of from about 0 to about 72 hours, most preferably about 24 hours.

A preferred oxirane compound is a diepoxide having the following general structure:

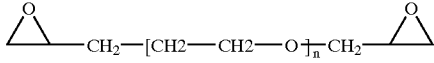

wherein n is from about 1 to about 50. Preferred epoxides include DER™ 332 and DER™ 736, available from the Dow Chemical Company.

A similar reaction occurs when a diepoxide reacts with cysteine residues:

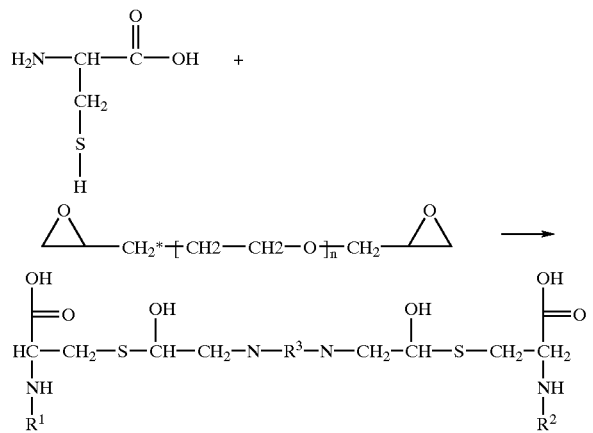

wherein $R^1$ and $R^2$ are the remainder of a first protein molecule and $R^3$ and $R^4$ are the remainder of a second protein molecule.

Persons of ordinary skill in the art will recognize that many of the crosslinking agents described herein will react with a variety of amino acid residues having pendant groups comprising a reactive nitrogen atom, sulfur atom, or oxygen atom. Hence, one end of a diepoxide may react with a cysteine residue while the other end of the diepoxide reacts with an arginine residue, as follows:

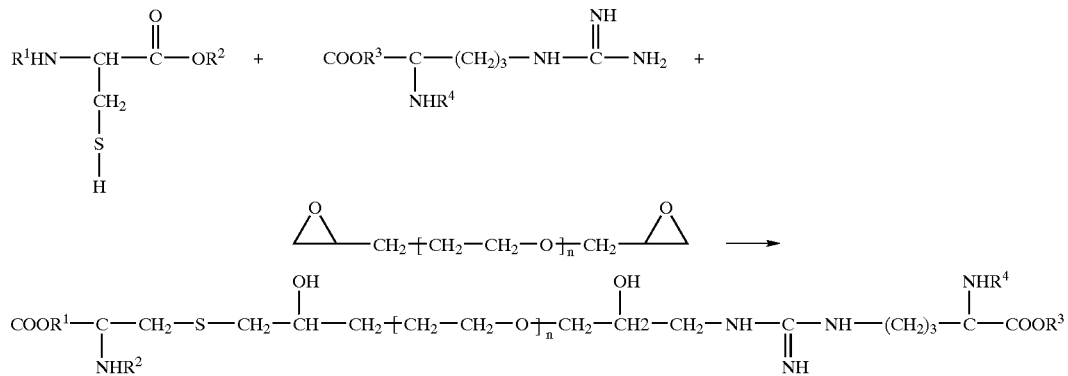

The identity of amino acid residues linked by the crosslinking agent is not as important as the requirement that a sufficient quantity of crosslinking between protein molecules occurs to produce a film having desired properties. In a preferred embodiment, the crosslinking produces an elastomeric film.

Network Properties

As seen below, a three dimensional keratin-based network can be formed using a variety of chemistries. Preferably, the "dissolution rate" of such a network is controllable by controlling the crosslink density of the film and the level and type of functionality, particularly the functionality adjacent to the crosslink site. For example, the use of a crosslinking agent having one of the following characteristics reduces the dissolution rate of the resulting network: a crosslinking agent which forms S—C bonds, as opposed to more hydrolyzable bonds, such as ester bonds; a crosslinking agent which introduces substantial steric hindrance at the crosslink site; a crosslinking agent which is hydrophobic. The "dissolution rate" of the resulting network or film is measured by determining how long the film resists hydrolysis upon exposure to an aqueous buffer having a pH of about 7. A desirable "dissolution rate" will depend upon the application in which the film is to be used.

The invention will be better understood with reference to the following Examples, which are illustrative only:

EXAMPLE 1

Reduced, HMWK was prepared by placing 40 g of clean, dry human hair into a 1000 mL wide mouth glass reactor. 800 mL of a 0.8M solution of thioglycolic acid at pH 10.2 (adjusted with potassium hydroxide) was added and the mixture was stirred at room temperature under a nitrogen atmosphere for 18 hours. The solution was filtered and the liquid discarded. The hair was rinsed with copious amounts of deionized (DI) water, then placed back into the reactor. 400 mL of a 7M urea solution was added and the mixture was stirred at room temperature under a nitrogen atmosphere for 24 hours. After urea extraction, the solids were separated from the liquid by centrifugation. The liquid was added dropwise to a 10-fold volume excess of ethanol, thereby forming a keratin precipitate. The precipitated keratins were isolated by filtration and dried under vacuum. The resulting HMWK powder was ground by hand using a mortar and pestle.

EXAMPLE 2

500 g of clean, dry human hair was placed in a 12000 mL round bottom flask. 8350 mL of 1 weight/volume percent of hydrogen peroxide was added and the reaction heated to reflux for 180 minutes. The hair was separated from the liquid by filtration and the liquid discarded. The hair was rinsed with copious amounts of water and allowed to air dry. 100 g of the dried, oxidized hair was placed in a 2000 mL round bottom flask. 1000 mL of 1M thioglycolic acid at pH 9 (adjusted with ammonium hydroxide) was added and the mixture was heated to 60° C. under a nitrogen atmosphere for 24 hours. After reductive extraction, the solids were separated from the liquid by centrifugation. The liquid was added dropwise to a 8-fold volume excess of ethanol, thereby forming a keratin precipitate. The precipitated HMWK keratins were isolated by filtration and dried under vacuum.

A solution was prepared by mixing 2 g of HMWK with 1 mL of 30% ammonium hydroxide and 10 mL of dimethyl sulfoxide. The solution was stirred and heated to ca. 75° C. to effect dissolution of the keratins. The solution was split into 4 volumes and placed into separate vials. To each of these 4 solutions was added 5, 10, 15, and 20 weight percent (relative to HMWK) of hexanediisocyanate, respectively, and 0.05, 0.1, 0.15, and 0.2 weight percent (relative to HMWK) of butyldilauryltin catalyst, respectively. The solutions were mixed using a vortex mixer, poured into separate petri dishes, and placed under a heat lamp. After 120 minutes of exposure, the samples were removed from the heat and peeled from the petri dishes. After curing, a small piece of each elastomer was immersed in a pH 7 aqueous buffer solution. After exposure to aqueous buffer for 48 hours, elastomers made with 5, 15, and 20 weight percent hexanediisocyanate were unchanged. The sample made with 10 weight percent hexanediisocyanate began to slowly hydrolyze after only 24 hours.

EXAMPLE 3

4.5 g of the HMWK sample from Example 2 was dissolved in 2.25 mL of 30% ammonium hydroxide and 22.5 mL of dimethyl sulfoxide by heating to ca. 75° C. and stirred. The solution was split into 9 separate vials and used to prepare the solutions described in the following Table.

| Sample | Terephthalic Acid (grams) | Phthalic Anhydride (grams) | DER ™ 332 Resin (grams) | Sodium Acetate Catalyst (grams) |
|---|---|---|---|---|
| 1a (control) | — | — | — | — |
| 2a | 0.025 | — | — | 0.005 |
| 2b | 0.050 | — | — | 0.005 |
| 3a | — | 0.025 | — | 0.005 |
| 3b | — | 0.050 | — | 0.005 |
| 4a | — | — | 0.025 | — |
| 4b | — | — | 0.050 | — |

The solutions were poured into separate petri dishes and placed under a heat lamp for ca. 240 minutes. After curing, a small piece of each elastomer was immersed in a pH 7 aqueous buffer solution. After exposure to aqueous buffer for 48 hours, elastomers 1a, 2a, 2b, 3a, and 3b had disintegrated and partially dissolved. After 6 days, elastomers 4a and 4b remained intact.

Persons of ordinary skill in the art will recognize that many modifications may be made to the present invention without departing from the spirit and scope of the present invention. The embodiment described herein is meant to be illustrative only and should not be taken as limiting the invention, which is defined in the claims.

I claim:

1. A method for making a keratin elastomer comprising contacting a solution of keratin proteins with a difunctional isocyanate cross-linking agent under conditions effective to cross-link the keratin proteins, wherein the elastomer is stable in an aqueous buffer having a pH of about 7 for at least 7 days.

2. The method of claim 1, wherein the difunctional isocyanate cross-linking agent is hexanediisocyanate.

3. A method for making a keratin elastomer comprising contacting a solution of keratin proteins with a difunctional epoxide cross-linking agent under conditions effective to cross-link the keratin proteins, wherein the elastomer is stable in an aqueous buffer for at least 6 days.

4. The method of claim 3 wherein the crosslinking agent is a diepoxide resin having the following general structure:

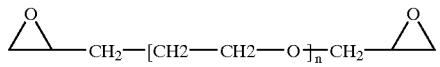

wherein n is from about 1 to about 50.

5. A method for making a keratin elastomer comprising contacting a solution of keratin proteins with an anhydride under conditions effective to cross-link the keratin proteins, wherein the elastomer is stable in an aqueous buffer for at least 6 days.

6. The method of claim 5, wherein the anhydride is phthalic anhydride.

7. A keratin elastomer comprising keratin proteins cross-linked by a difunctional isocyanate cross-linking agent, wherein the elastomer is stable in an aqueous buffer having a pH of about 7 for at least 7 days.

8. The elastomer of claim 7, wherein the difunctional isocyanate cross-linking agent is hexanediisocyanate.

9. A keratin elastomer comprising keratin proteins cross-linked with a difunctional epoxide cross-linking agent, wherein the elastomer is stable in an aqueous buffer for at least 6 days.

10. The keratin elastomer of claim 9 wherein the crosslinking agent is a diepoxide resin having the following general structure:

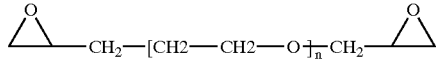

wherein n is from about 1 to about 50.

11. A keratin elastomer comprising keratin proteins cross-linked with an anhydride, wherein the elastomer is stable in an aqueous buffer for at least 6 days.

12. The elastomer of claim 11, wherein the anhydride is phthalic anhydride.

* * * * *